(12) United States Patent
Andritz

(10) Patent No.: US 6,389,609 B1
(45) Date of Patent: May 21, 2002

(54) UNIVERSAL STONE CATCHER URINAL SYSTEM

(76) Inventor: Stephen J. Andritz, 3433 Constance St., Titusville, FL (US) 32796

( * ) Notice: Subject to any disclaimer, the term of this patent is extended or adjusted under 35 U.S.C. 154(b) by 72 days.

(21) Appl. No.: 09/626,379

(22) Filed: Jul. 26, 2000

Related U.S. Application Data

(60) Provisional application No. 60/147,473, filed on Aug. 9, 1999.

(51) Int. Cl.[7] .............................................. A47K 11/12
(52) U.S. Cl. ...................................... 4/144.1; 604/317
(58) Field of Search .......................... 4/144.1–144.4; 604/317, 318, 329, 347, 349

(56) References Cited

U.S. PATENT DOCUMENTS

| | | | | |
|---|---|---|---|---|
| 703,131 A | * | 6/1902 | Jaenel | 4/144.3 |
| 2,896,788 A | * | 7/1959 | Hoffberger | |
| 3,473,172 A | | 10/1969 | Friedman et al. | |
| 3,711,871 A | * | 1/1973 | Sherin | 4/144.1 |
| 3,811,136 A | * | 5/1974 | Whitney et al. | 4/144.1 |
| 3,894,845 A | * | 7/1975 | McDonald | |
| 3,927,426 A | | 12/1975 | Geddes | |
| 4,241,017 A | * | 12/1980 | Balistreri et al. | 4/144.1 |
| 4,559,649 A | | 12/1985 | Burnett | |
| 4,769,858 A | * | 9/1988 | Gamm et al. | 4/144.1 |
| 4,889,249 A | * | 12/1989 | Hulon | 4/144.1 |
| RE33,686 E | * | 9/1991 | Parrish | 604/318 |
| 5,125,118 A | | 6/1992 | Green | |
| 5,331,689 A | * | 7/1994 | Haq | 4/144.1 |
| 5,411,495 A | * | 5/1995 | Willingham | 604/329 |
| 5,762,071 A | * | 6/1998 | Newman et al. | 604/329 |

* cited by examiner

Primary Examiner—Charles R. Eloshway
(74) Attorney, Agent, or Firm—Patent & Trademark Services; Joseph H. McGlynn

(57) ABSTRACT

A urine basin which has head attachments for males and females. In addition, the basin has a filter for capturing kidney stones and a handle for carrying the basin.

10 Claims, 1 Drawing Sheet

UNIVERSAL STONE CATCHER URINAL SYSTEM

Applicant claims priority of Provisional Ser. No. 60/147,473, filed Aug. 9, 1999.

BACKGROUND OF THE INVENTION

This invention relates, in general, to urinals, and, in particular, to urinals which assist in the capturing of kidney stones.

DESCRIPTION OF THE PRIOR ART

In the prior art various types of have been proposed. For example, U.S. Pat. No. 3,473,172 to Friedman et al discloses a female urinal with a tapered opening at the top of a collection basin.

U.S. Pat. No. 3,927,426 to Geddes discloses a urinal with a detachable handle and a removable cap.

U.S. Pat. No. 4,559,649 to Burnett discloses a urine collection system with a removable, tapered upper collection fixture.

U.S. Pat. No. 5,125,118 to Green discloses a urine collection system with a tapered opening designed for use by women.

SUMMARY OF THE INVENTION

The present invention is directed to a urine basin which has head attachments for males and females. In addition, the basin has a filter for capturing kidney stones and a handle for carrying the basin.

It is an object of the present invention to provide a new and improved urinal basin.

It is an object of the present invention to provide a new and improved urinal basin which will assist medical personnel in capturing kidney stones.

It is an object of the present invention to provide a new and improved urinal basin which is easily used by either a man or a women.

These and other objects and advantages of the present invention will be fully apparent from the following description, when taken in connection with the annexed drawings.

DESCRIPTION OF THE PREFERRED EMBODIMENT

Figure 1:
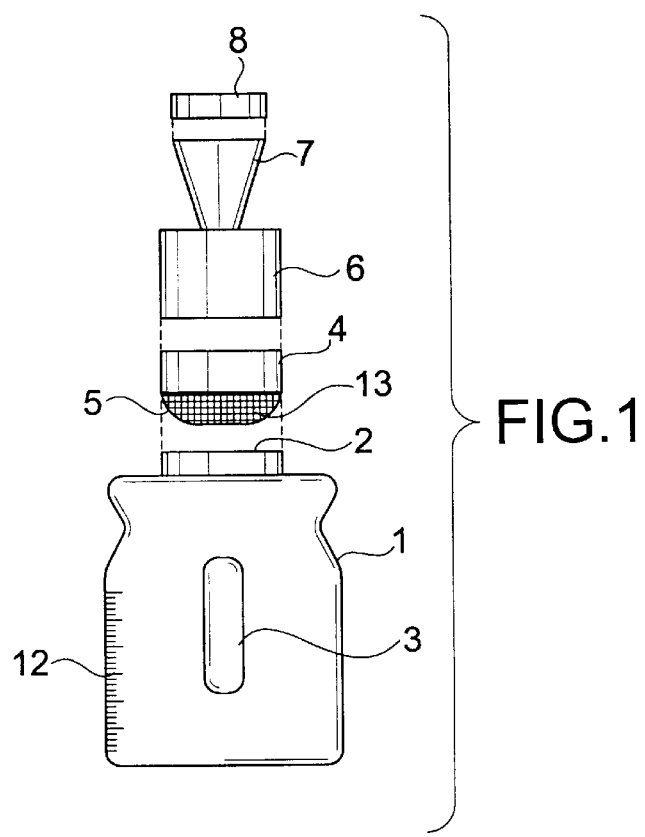
FIG. 1 is an exploded front plan view of the male version of the present invention.

Referring now to the drawings in greater detail, FIG. 1 shows an exploded view of the present invention. The invention comprises both a male version (shown in FIGS. 1 and 2) and a female version (shown in FIGS. 1 and 2). The male version is shown in FIG. 1 and comprises a basin 1 having an open top 2 and a handle 3 on the side of the basin 1. Above the basin 1 a filter 4, 5 is shown. The filter is designed to be used in facilities such as hospitals to capture items such as kidney stones that are passed in the urine of a patient. The basin 1 is preferably made from clear plastic and has graduated lines 12 along he side so technicians could measure the amount of liquid in the basin 1.

The filter has a top portion 4 which will sit on top of the opening 2 in the basin 1. Attached at the bottom of the top portion 4 is a filter screen 5 which will sit within the open top 2 of the basin 1. The filter screen 5 can be made from any material suitable for the intended purpose, however, plastic is the preferred material. The screen 5 should have a fine mesh which will allow urine to pass through into the basin 1, however, the openings in the mesh should be small enough to trap any kidney stones which are present in the patient's urine. In addition, the filter 5 could be provided with a litmus strip 13, in any conventional manner, which would detect the presence of blood in the urine.

Figure 2:
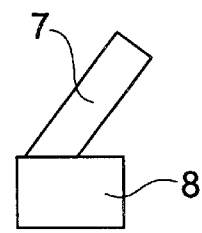
FIG. 2 is a side view of the male top of the present invention.

Located above the filter is a male top 6, 7 (also shown in FIG. 8). The male top has an upper portion 7, which as shown in FIG. 2, is angled starting at the top of the upper portion down toward the bottom portion 6 to make it convenient for a male to use the invention. Also, as shown in FIG. 1, the upper portion 7 is tapered to prevent flashback when used by a male patient. The bottom portion 6 will engage the top of the filter 4 and be secured in that position for use by male patients. How the bottom portion 6 engages the top portion 4 of the filter is not material as long as the two items are secured to one another. For example, the bottom portion 6 could fit snugly inside the top portion 4 of the filter, or it could fit outside the top portion 4 of the filter.

Positioned on top of the top portion 7 is a cap which engages the top of the bottom portion 7 to prevent the urine from accidentally spilling. How the cap 8 engages the top portion 7 is not material as long as the two items are secured to one another. For example, the cap 8 could fit snugly inside the top portion 7, or it could fit outside the top portion 7. It could be secured with a friction fit or the cap could be made from a resilient material which can be squeezed over or into the top portion 7.

Figure 3:
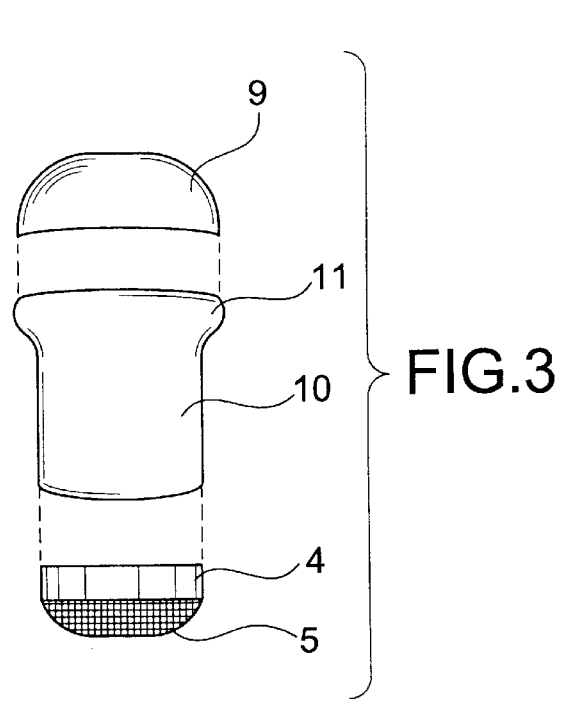
FIG. 3 is an exploded front plan view of the female version of the present invention without the basin.
Figure 4:
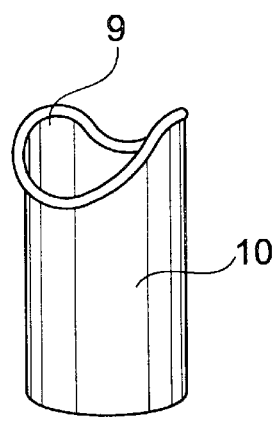
FIG. 4 is a perspective view of the female top of the present invention.

The female version of the present invention is shown in FIGS. 3 and 4. It should be noted that the female version uses the same basin 1 as the male version, however, the basin 1 has not been shown in FIG. 3 for clarity. The same filter 4, 5 as is used in the male version will also be used in the female version. The filter has a top portion 4 which will sit on top of the opening 2 in the basin 1. Attached at the bottom of the top portion 4 is a filter screen 5 which will sit within the open top 2 of the basin 1. The filter screen 5 can be made from any material suitable for the intended purpose, however, plastic is the preferred material. The screen 5 should have a fine mesh which will allow urine to pass through into the basin 1, however, the openings in the mesh should be small enough to trap any kidney stones which are present in the patient's urine.

Above the filter is a female top 10 which has a flared upper portion 11, forming a channel, which will make it convenient for a female to use the present invention by directing the urine into the top 10 and then into the basin 1. A cap 9 with a complimentary shape to the top of the female top is placed onto the female top 1 1 and serves the same purpose as the male cap 8, as explained above. However, the female cap 9 is shaped to fit within the top of the female top 10. The female cap 9 can be secured by friction, or it can be made resilient enough to be squeezed into the top of the female top 10 in order to secure the cap to the top.

It should be noted that the urinal system of the present invention would include the basin 1, the filter 4, 5, the male top 6, 7, the female top 10, 11, the cap 8, and the cap 9. This way the user could select whichever top and cap was suitable for the user. In addition, the urinal system of the present invention is not solely limited to use in hospitals. It could also be used in activities such as camping trips where normal bathroom facilities are not available. Of course, the system does not have to be used with the filter 4, 5 if trapping kidney stones is not a priority.

Although the Universal Stone Catcher Urinal System and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A urinal system comprising:

a container for collecting a liquid, said container having a bottom, an open top and sides, a filter secured to said open top, said filter having a bottom and an open top, the bottom being located within said container and the open top being located outside said container, a first top means for assisting a male to deposit urine into said container, a second top means for assisting a female to deposit urine into said container, each of said first and second top means having an open bottom and an open top, first cap means for closing said open top of said first top means, and second cap means for closing said open top of said second top means.

2. The urinal system as claimed in claim 1, wherein said container has a handle on at least one of said sides.

3. The urinal system as claimed in claim 1, wherein said container has graduation marks on at least one of said sides.

4. The urinal system as claimed in claim 1, wherein said filter bottom is a fine mesh.

5. The urinal system as claimed in claim 1, wherein said filter bottom has a means for detecting the presence of blood in urine.

6. The urinal system as claimed in claim 5, wherein said means for detecting the presence of blood in urine is a litmus strip.

7. The urinal system as claimed in claim 1, wherein said first top means makes an acute angle from a top of said top means to a bottom of said top means.

8. The urinal system as claimed in claim 1, wherein said first top means is tapered from a top of said first top means to a bottom of said first top means.

9. The urinal system as claimed in claim 8, wherein said taper is wider adjacent a top of said first top means than adjacent a bottom of said first top means.

10. The urinal system as claimed in claim 1, wherein said second top means is wider adjacent a top of said second top means than at a bottom of said second top means.

* * * * *